United States Patent
Vogt et al.

(10) Patent No.: US 11,266,762 B2
(45) Date of Patent: Mar. 8, 2022

(54) METHODS AND KITS FOR PRODUCING A FIBRIN MATRIX

(71) Applicant: Kuros Biosurgery AG, Schlieren (CH)

(72) Inventors: Lorenz Vogt, Baeretswil (CH); Alistair Simpson Irvine, Hausen am Albis (CH); Philippe Paul Saudan, Pfungen (CH)

(73) Assignee: KUROS BIOSURGERY AG, Schlieren (CH)

( * ) Notice: Subject to any disclaimer, the term of this patent is extended or adjusted under 35 U.S.C. 154(b) by 274 days.

(21) Appl. No.: 16/294,698

(22) Filed: Mar. 6, 2019

(65) Prior Publication Data

US 2019/0275197 A1     Sep. 12, 2019

Related U.S. Application Data

(60) Provisional application No. 62/640,814, filed on Mar. 9, 2018.

(30) Foreign Application Priority Data

Mar. 16, 2018    (EP) .................................... 18162280

(51) Int. Cl.
    *A61L 24/10*     (2006.01)
    *A61L 27/22*     (2006.01)
    *A61L 27/54*     (2006.01)

(52) U.S. Cl.
    CPC ........... *A61L 24/106* (2013.01); *A61L 24/102* (2013.01); *A61L 27/54* (2013.01); *A61L 27/225* (2013.01);
(Continued)

(58) Field of Classification Search
    CPC ...... A61L 24/106; A61L 27/54; A61L 24/102; A61L 2300/414; A61L 2430/02; A61L 2430/38; A61L 27/225; A61L 2300/412
See application file for complete search history.

(56) References Cited

U.S. PATENT DOCUMENTS

| 7,247,609 B2 * | 7/2007 | Lutolf | ................... | A61L 27/225 |
| | | | | 514/1.1 |
| 8,034,618 B2 * | 10/2011 | Lutolf | ................... | A61L 27/227 |
| | | | | 435/395 |

(Continued)

FOREIGN PATENT DOCUMENTS

| AU | 2006204461 C1 * | 1/2012 | ........... C07K 14/635 |
| EP | 1465989 | 10/2004 | |

(Continued)

OTHER PUBLICATIONS

Besson, et al., "Synthetic Peptide Substrates for a Conductimetric Assay of Pseudomonas aeruginosa Elastase," Analytical Biochemistry, 237, pp. 216-223 (1996).

(Continued)

*Primary Examiner* — Louise W Humphrey
*Assistant Examiner* — Anjali Ajit Hirani
(74) *Attorney, Agent, or Firm* — Pabst Patent Group LLP

(57) ABSTRACT

Methods for producing a fibrin matrix comprising a fusion peptide are described herein. In some embodiments, the method includes providing three different components, including a first component containing fibrinogen or a fibrinogen precursor and optionally, transglutaminase or a transglutaminase precursor, a second component containing thrombin or a thrombin precursor, and a third component containing a fusion peptide. In these embodiments, neither the first component nor the second component includes the fusion peptide. In some embodiments, the first or second components are premixed with the third component. The first, second and third components are mixed to form a fibrin matrix comprising a covalently linked fusion peptide. The mixing is carried out in a time frame of not more than 5 days.

(Continued)

A kit for producing the fibrin matrix comprising a covalently linked fusion peptide is also described herein.

27 Claims, 6 Drawing Sheets

Specification includes a Sequence Listing.

(52) U.S. Cl.
CPC ... *A61L 2300/412* (2013.01); *A61L 2300/414* (2013.01); *A61L 2430/02* (2013.01); *A61L 2430/38* (2013.01)

(56) References Cited

U.S. PATENT DOCUMENTS

| | | | | |
|---|---|---|---|---|
| 8,226,942 | B2 * | 7/2012 | Charier | A61K 38/47 424/94.64 |
| 8,318,674 | B2 * | 11/2012 | Schense | A61P 19/10 514/11.8 |
| 8,575,101 | B2 * | 11/2013 | Schense | A61L 27/427 514/11.8 |
| 10,589,001 | B2 * | 3/2020 | Schense | A61L 27/46 |
| 2004/0082513 | A1 * | 4/2004 | Hubbell | A61L 31/046 435/193 |
| 2006/0148704 | A1 | 7/2006 | Schense | |
| 2012/0234718 | A1 * | 9/2012 | Schense | A61L 27/225 206/524.1 |
| 2013/0183279 | A1 * | 7/2013 | Muller-Maissen | A61L 27/54 424/94.3 |

FOREIGN PATENT DOCUMENTS

| | | | | |
|---|---|---|---|---|
| EP | 2686027 | A1 * | 1/2014 | A61L 27/227 |
| EP | 1833505 | B1 * | 4/2014 | A61P 35/00 |
| EP | 1833522 | B1 * | 6/2016 | A61P 19/00 |
| JP | 2013173770 | A * | 9/2013 | A61L 27/227 |
| WO | 2003052091 | | 6/2003 | |

OTHER PUBLICATIONS

Coombs, et al., "Directing Sequence-specific Proteolysis to New Targets. The influence of loop size and target sequence on selective proteolysis by tissue-type plasminogen activator and urokinase-type plasminogen activator," The Journal of Biological Chemistry, vol. 273, pp. 4323-4328 (1998).

Netzel-Arnett, et al., "Sequence Specificities of Human Fibroblast and Neutrophil Collagenases," The Journal of Biological Chemistry, vol. 266, pp. 6747-6755, (1991).

Smith, et al., "Rapid Identification of Highly Active and Selective Substrates for Stromelysin and Matrilysin Using Bacteriophage Peptide Display Libraries," The Journal of Biological Chemistry, vol. 270, pp. 6440-6449, (1995).

Takagi and Doolittle, "Amino Acid Sequence Studies on the alpha Chain of Human Fibrinogen. Location of Four Plasmin Attack Points and a Covalent Cross-Linking site," Biochemistry, vol. 14, pp. 5149-5156, (1975).

European Search Report for EP 18162280.4 dated Oct. 9, 2018.

* cited by examiner

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 1

Gly Ala Lys Asp Val
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 2

Lys Lys Lys Lys
1

<210> SEQ ID NO 3
<211> LENGTH: 16
<212> TYPE: PRT
<213> ORGANISM: Artificial Sequence
<220> FEATURE:
<223> OTHER INFORMATION: synthetic polypeptide

<400> SEQUENCE: 3

Tyr Arg Gly Asp Thr Ile Gly Glu Gly Gln Gln His His Leu Gly Gly
1               5                   10                  15

<210> SEQ ID NO 4
<211> LENGTH: 8
<212> TYPE: PRT
<213> ORGANISM: Artificial Sequence
<220> FEATURE:
<223> OTHER INFORMATION: synthetic polypeptide
```

```
<400> SEQUENCE: 4

Asn Gln Glu Gln Val Ser Pro Leu
1               5

<210> SEQ ID NO 5
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 5

Leu Ile Lys Met Lys Pro
1               5

<210> SEQ ID NO 6
<211> LENGTH: 6
<212> TYPE: PRT
<213> ORGANISM: Artificial Sequence
<220> FEATURE:
<223> OTHER INFORMATION: synthetic polypeptide

<400> SEQUENCE: 6

Asn Phe Lys Ser Gln Leu
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: ACETYLATION

<400> SEQUENCE: 7

Gly Pro Leu Ala Leu Thr Ala Leu
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic polypeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: AMIDATION

<400> SEQUENCE: 8

Pro Phe Glu Leu Arg Ala
1               5

<210> SEQ ID NO 9
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: MISC_FEATURE
```

```
<222> LOCATION: (1)..(1)
<223> OTHER INFORMATION: carbobenzoxy modification
<220> FEATURE:
<221> NAME/KEY: MOD_RES
<222> LOCATION: (4)..(4)
<223> OTHER INFORMATION: AMIDATION

<400> SEQUENCE: 9

Ala Ala Phe Ala
1

<210> SEQ ID NO 10
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 10

Gly Pro Leu Gly Ile Ala Gly Pro
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 11

Pro His Tyr Gly Arg Ser Gly Gly
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 12

Pro Gly Ser Gly Arg Ser Ala Ser Gly
1               5

<210> SEQ ID NO 13
<211> LENGTH: 4
<212> TYPE: PRT
<213> ORGANISM: Homo sapiens

<400> SEQUENCE: 13

Tyr Lys Asn Arg
1

<210> SEQ ID NO 14
<211> LENGTH: 46
<212> TYPE: PRT
<213> ORGANISM: Artificial Sequence
<220> FEATURE:
<223> OTHER INFORMATION: Synthetic fusion protein

<400> SEQUENCE: 14

Asn Gln Glu Gln Val Ser Pro Leu Tyr Lys Asn Arg Ser Val Ser Glu
1               5                   10                  15

Ile Gln Leu Met His Asn Leu Gly Lys His Leu Asn Ser Met Glu Arg
            20                  25                  30

Val Glu Trp Leu Arg Lys Lys Leu Gln Asp Val His Asn Phe
```

```
                        35                  40                  45

<210> SEQ ID NO 15
<211> LENGTH: 42
<212> TYPE: PRT
<213> ORGANISM: Artificial Sequence
<220> FEATURE:
<223> OTHER INFORMATION: Synthetic fusion protein

<400> SEQUENCE: 15

Asn Gln Glu Gln Val Ser Pro Leu Ser Val Ser Glu Ile Gln Leu Met
1               5                   10                  15

His Asn Leu Gly Lys His Leu Asn Ser Met Glu Arg Val Glu Trp Leu
            20                  25                  30

Arg Lys Lys Leu Gln Asp Val His Asn Phe
            35                  40
```

METHODS AND KITS FOR PRODUCING A FIBRIN MATRIX

CROSS-REFERENCE TO RELATED APPLICATION

This application claims benefit of and priority to U.S. Application No. 62/640,814 filed on Mar. 9, 2018 and European Application No. 18162280.4 filed on Mar. 16, 2018, the disclosures of which are incorporated by reference herein.

REFERENCE TO SEQUENCE LISTING

The Sequence Listing submitted as a text file named "KUROS_160_ST25.txt," created on Feb. 19, 2019, and having a size of 3,954 bytes is hereby incorporated by reference pursuant to 37 C.F.R. § 1.52(e)(5).

FIELD OF THE INVENTION

The present invention relates to a method and a kit for producing fibrin matrix with a fusion peptide and to a fibrin matrix with a fusion peptide.

BACKGROUND OF THE INVENTION

Fibrin sealants such as ARTISS® or TISSEEL®, both from Baxter Healthcare AG, are known products for the use in tissue repair. ARTISS® and TISSEEL® consist of two components that are mixed immediately prior to, or during, the application. One component contains fibrinogen, factor XIII and aprotinin while the other component contains thrombin. Upon mixing the two components, thrombin on one hand cleaves fibrinogen leading to fibrin polymers and on the other hand activates Factor XIII to form Factor XIIIa, a transglutaminase which crosslinks fibrin polymers to form a solid fibrin matrix.

A fibrin matrix is the product of a process in which fibrinogen is cleaved by thrombin and the resulting fibrin polymers crosslink in the presence of a calcium ion source and Factor XIIIa to form a three-dimensional network.

It is known that certain bioactive factors may promote bone repair. Parathyroid hormone (PTH) is an 84 amino acid peptide that is made and secreted by the parathyroid gland. This hormone plays a primary role in controlling serum calcium levels through its action on various tissues, in particular bones. This makes PTH particularly interesting for the treatment of bone disorders.

Approaches have been undertaken to combine the fibrin sealant ARTISS or TISSEEL® with PTH. For example, U.S. Pat. No. 8,034,618 B2 describes the mixing of a fusion protein containing PTH with either the fibrinogen or thrombin solution, referred to in this application as "pre-mixing". To form the fibrin matrix, the diluted precursor-solution containing the fusion protein and fibrinogen was injected into the second precursor-solution containing the thrombin at room temperature. The mixture is then applied to the site of the bone disorder and forms a fibrin matrix. The bioactive factor, PTH, is released from the matrix and triggers regeneration of the bone tissue locally.

Surprisingly, it was found, that the fusion peptide containing PTH in a fibrinogen solution degrades over a relatively short period of time at room temperature (Example 1). This is in particular surprising since the fibrinogen solution of ARTISS® and TISSEEL® contain aprotinin. It was expected that aprotinin would prevent any proteolysis of the compounds. However, it was observed, that exposure of the fusion peptide to the fibrinogen solution for more than 5 days at room temperature caused a substantial degradation of the fusion peptide containing PTH. Since the degradation occurs in a time frame typically needed for industrial manufacturing of a tissue sealant, the approach used in the aforementioned prior art to produce a fibrin matrix containing the fusion peptide has severe drawbacks as to reproducibility and consistency.

SUMMARY OF THE INVENTION

Methods for producing a fibrin matrix comprising a fusion pep-tide are described herein. In some embodiments, the method includes providing three different components, including a first component containing fibrinogen or a fibrinogen precursor and optionally, transglutaminase or a transglutaminase precursor, a second component containing thrombin or a thrombin precursor, and a third component containing a fusion peptide. In these embodiments, neither the first component nor the second component includes the fusion peptide. In some embodiments, the first or second components are premixed with the third component. The first, second and third components are mixed to form a fibrin matrix comprising a covalently linked fusion peptide. The mixing is carried out in a time frame of not more than 5 days. A kit for producing the fibrin matrix comprising a covalently linked fusion peptide is also described herein.

DETAILED DESCRIPTION OF THE INVENTION

Figure 1A:
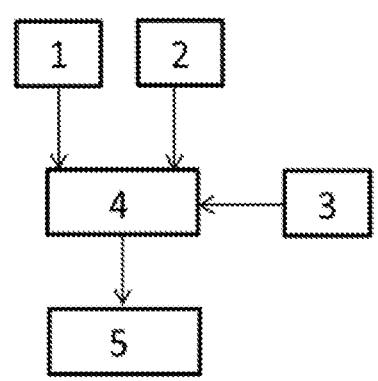
FIGS. 1A, 1B, and 1C are flow diagrams of the steps of three exemplary methods described herein.

I. Methods for Producing a Fibrin Matrix

Methods for producing a fibrin matrix comprising a fusion peptide are disclosed. The method comprises a first step (i) of providing a first component including fibrinogen or a fibrinogen precursor and a transglutaminase, such as Factor XIIIa, or a transglutaminase precursor, such as Factor XIII, and a second step (ii) of providing a second component including thrombin or a thrombin precursor. Neither the first component nor the second component comprises a fusion peptide comprising a first domain and a covalently cross-linkable transglutaminase substrate domain in a second domain. The method further comprises a third step (iii) of providing a third component including the fusion peptide comprising a first domain and a covalently crosslinkable transglutaminase substrate domain in a second domain. The third component does not include fibrinogen or a fibrinogen precursor nor thrombin or a thrombin precursor. In a further fourth step (iv) of the method, a fibrin matrix comprising a covalently linked fusion peptide is formed by mixing the first, second and third components. The mixing of the three components is carried out in a time frame of not more than 5 days, preferably 2 to 3 days and most preferably 1 day. Optionally, the three components are mixed together in a time frame of even less than 1 day, such as within 10 hours, 5 hours, 4, hours, 3 hours, or 2 hours; within less than 60 minutes, such as within 30 minutes, 20 minutes, 10 minutes, or 5 minutes; or even within less than 60 seconds, such as within 40 seconds, 30 seconds, 20 seconds, 10 seconds, or 5 seconds.

Optionally, the second component is added to a mixture of the first and third components or that the first component is added to a mixture of the second and third components in a time frame of not more than 5 days, preferably not more than 2 days, most preferably not more than 1 day. For example, the first component (e.g. including fibrinogen or a fibrinogen precursor and a transglutaminase or a transglutaminase precursor) and the third component (including the fusion peptide) could be mixed together, then stored for up to 5 days, preferably for up to 2 to 3 days and most preferably for up to 1 day, and then mixed with the second component (including thrombin or a thrombin precursor). Similarly, the second component (including thrombin or a thrombin precursor) and the third component (including the fusion peptide) could be mixed together, then stored for up to 5 days, preferably for up to 2 to 3 days and most preferably for up to 1 day, and then mixed with the first component (e.g. including fibrinogen or a fibrinogen precursor and a transglutaminase or a transglutaminase precursor).

In embodiments in which the first and second components are mixed together in step (iv), preferably the third component is added to the mixture either at the time of mixing the first and second components or within a time frame of not more than 1 day, preferably within 1 hour, preferably within 5 minutes, preferably within 1 minute, most preferably within 30 seconds of mixing the first and second components. In this embodiment, the mixture of the three components is administered to a patient within five days of initiation of mixing the three components, depending on the method of administration.

In some embodiments the components are mixed using a connecting device. A connecting device can be used to allow mixing of two or three components by either mixing in the connecting device or allowing the transfer of two or more components into a single container through the connecting device.

In some embodiments, the fibrin matrix is formed in situ in or on the body. In other embodiments, the matrix can be formed outside the body and then applied in the preformed shape. In both cases the matrix is applied or implanted at the site in need of treatment.

Two pre-mixed components can be in one compartment of a two compartment device and the remaining component can be in a second compartment of the device, preferably the compartments are attached via a connecting device. A device containing two or more compartments can be replaced with the same number of separate containers as the number of compartments in the device and be used in the same manner as the multi-compartment device described herein.

Two components can be in a dual compartment device (or two containers) and the remaining component can be in a third compartment (or third container). The two components of the dual compartment device are mixed through a connecting device which then connects the third compartment leading to the mixing of the three components. Preferably the dual compartment and third compartments are connected by a connecting device. The connecting device may be a separate device or may be part of the dual compartment device or part of the third compartment. Optionally, the three components may be further mixed by attaching the third compartment to a fourth compartment and transferring the mixture back and forth between the third and fourth compartments. The third and fourth compartments may be attached by a connecting device (see, e.g., FIG. 2E).

The three components may be in separate compartments and mixed simultaneously by attaching to a three-way connecting device or may be in a three compartment syringe. Preferably the three compartments are connected to a connecting device (see, e.g., FIGS. 2A-2D and 4B-4C) or have a connecting device as part of one of the three separate compartments or have a connecting device as part of a three compartment syringe.

Alternatively, the three components are in three independent compartments. In a first step, two of the three components are mixed and in a second step this mixture is mixed with the remaining component (see, e.g., FIGS. 3A-3D and FIGS. 5A-5E). The respective compartments may be connected with connecting devices and mixing achieved by transferring the mixture back and forth between the compartments.

The thrombin precursor can be Prothrombin. Prothrombin is activated by a complex containing Factor Va and Factor Xa.

Mixing of the components can occur at an ambient temperature, such as between 15° C. and 40° C., preferably at 20° C. to 37° C.

Mixtures of two components, such as a mixture containing component 3 and component 2 or a mixture containing component 3 and component 1, can be stored at 2° C. to 30° C. for up to five days following mixing.

Preferably, the initial fibrinogen concentration prior to mixing of the components is 10 to 200 mg per mL component solution, more preferably 30 to 150 mg per mL component solution and most preferably 72 to 110 mg per mL component solution; and the initial thrombin is 0.1 to 1500 IU per mL component solution, more preferably 0.5 to 500 IU per mL component solution and most preferably 2 to 7 IU per mL component solution. In the final mixture, the fibrinogen concentration is 8 to 160 mg per mL fibrin matrix, more preferably 25 to 100 mg per mL fibrin matrix and most preferably 30 to 60 mg per mL fibrin matrix. The thrombin concentration in the final mixture is 0.05 to 100 IU per mL fibrin matrix, more preferably 0.2 to 20 IU per mL fibrin matrix and most preferably 1 to 4 IU per mL fibrin matrix. I.U. stands for one international unit of thrombin and is defined as the activity contained in 0.0853 mg of the First International Standard of Human Thrombin.

Additionally, a calcium ion source is typically present in at least one of the components. Providing a source for calcium ions is required for the activation of Factor XIII by thrombin. The first component, the second component or the third component may further comprise a calcium ion source. Preferably, the calcium ion source is calcium chloride, most preferably in hydrated form ($CaCl_2 \cdot 2H_2O$). Preferably, the calcium chloride concentration is 0.5 to 5 mg per mL fibrin matrix, more preferably 1.5 to 3.5 mg per mL and most preferably 2.5 to 3 mg per mL. The concentration of calcium ion source in one of the component solutions is typically in the range of 1 to 10 mg per ml component solution, even more preferably from 3 to 7 mg per ml component solution, most preferably from 5 to 6 mg per ml component solution.

In the first component solution, preferably the transglutaminase (e.g., Factor XIIIa) or transglutaminase precursor (e.g., Factor XIII) is present in a concentration range from 0.1 to 100 I.U. per millilitre component solution for the transglutaminase or a concentration of transglutaminase precursor that if activated would produce transglutaminase in this activity range, more preferably from 0.5 to 60 I.U. per millilitre component solution for the transglutaminase or a concentration of transglutaminase precursor that if activated would produce transglutaminase in this activity range, and most preferably from 1 to 10 I.U. per millilitre component solution for the transglutaminase or a concentration of transglutaminase precursor that if activated would produce transglutaminase in this activity range.

Mixing the components in a time frame of up to 5 days has the advantage of avoiding degradation of the respective components, in particular degradation of the fusion peptide. At the same time, the same efficacy in binding of the fusion peptide to the fibrin matrix is observed compared to the pre-mixing procedure (Example 2).

A. PTH Fusion Peptides

The PTH fusion peptide contains at least two domains wherein the first domain comprises PTH and the second domain comprises a crosslinkable substrate domain. An advantage of using PTH in a first domain of a fusion peptide can be found in an improved regeneration of bone tissue. PTH modulates bone remodelling and subsequently can increase bone density.

The crosslinkable substrate domain is preferably covalently crosslinkable to the fibrin matrix during or after its formation. The crosslinkable substrate domain is preferably a domain for an enzyme, preferably, a substrate domain for a transglutaminase ("transglutaminase substrate domain"). The PTH fusion peptide may be produced recombinantly or by chemical synthesis. The PTH fusion peptide is preferably produced by chemical synthesis. The amino acid sequence of the PTH fusion peptide may also contain an enzymatic or hydrolytic cleavage site, such that the PTH can be released with little or no modification to its primary structure.

1. PTH

The PTH in the first domain of the PTH fusion peptide may be PTH1-84, PTH1-38, PTH1-34, PTH1-31, or PTH1-25, or any modified or allelic versions of PTH exhibiting bone forming properties. PTH1-84 refers to the human sequence, lower numbering accounts for truncated, modified and allelic versions of PTH, which exhibits bone formation properties and triggers regeneration of bone tissue.

Preferred truncated versions of PTH are PTH1-38, PTH1-34, PTH1-31 or PTH1-25. Most preferred is PTH1-34. Preferably the PTH is human PTH, although PTH from other sources, such as bovine PTH, may be suitable.

2. Transglutaminase Substrate Domains

Transglutaminases catalyse acyl-transfer reactions between the gamma-carboxamide group of protein bound glutaminyl residues and the epsilon-amino group of lysine residues, resulting in the formation of N-epsilon-(gamma-glutamyl)lysine isopeptide side chains bridges. Preferably, the transglutaminase substrate domain is a substrate for a tissue transglutaminase ("tissue transglutaminase substrate domain"). In a preferred embodiment, the substrate domain is a substrate domain for Factor XIIIa ("Factor XIIIa substrate domain").

Preferably, the transglutaminase precursor is Factor XIII Once it is mixed with thrombin, Factor XIII will be activated by thrombin proteolysis to Factor XIIIa. Thrombin further initiates the reaction by cleaving fibrinogen to fibrin. The Factor XIIIa then covalently crosslinks the fibrin to form a fibrin matrix.

Transglutaminase substrate domains and in particular, Factor XIIIa substrate domains are suitable to link the PTH fusion peptide to fibrin matrices during formation of the matrices. A PTH fusion peptide comprising a covalently crosslinkable transglutaminase substrate domain in the second domain may also be covalently crosslinked to fibrin by the transglutaminase Factor XIIIa.

Transglutaminase substrate domains suitable for use in making the PTH fusion peptides described herein have been described in detail including their amino acid sequences in WO 03/052091 (sequence listing), the content of which is herein incorporated by reference.

The crosslinkable substrate domain may include GAKDV (SEQ ID NO: 1), KKKK (SEQ ID NO: 2), YRGDTIGEGQQHHLGG (SEQ ID NO: 3), or NQEQVSPL (SEQ ID NO: 4).

A preferred Factor XIIIa substrate domain has an amino acid sequence of NQEQVSPL (SEQ ID NO: 4) (referred to herein as "TG").

3. Cleavage Sites of the Fusion Peptide

The fusion peptide may further comprise a cleavage (or degradation) site between the first and second domains, preferably an enzymatic cleavage (or degradation) site. The cleavage site allows the PTH to be released with little or no modification to the primary peptide sequence.

Enzymatic cleavage site may contain a certain amino acid sequence that is recognized by the respective enzyme. The sequence in the domains are substrates for enzymes that are involved in cell migration (e.g. substrates for enzymes such as collagenase, plasmin, matrix metalloproteinases or elastase) although suitable domains are not restricted to these sequences. Preferably, the enzymatic cleavage site is a plasmin cleavage site. Plasminogen, the proenzyme of plasmin, may be associated with fibrinogen. Optionally, the component comprising fibrinogen or a fibrinogen precursor (referred to herein as "the first component") further comprises plasminogen.

i. Enzymatic Cleavage Sites

Suitable proteolytic cleavage sites include substrates for collagenase, plasmin, elastase, stromelysin, or plasminogen activators. Exemplary substrates are listed below. N1-N5 denotes amino acids 1-5 positions toward the amino terminus of the protein from the site were proteolysis occurs. N1'-N4' denote amino acids 1-4 positions toward the carboxy terminus of the protein from the site where proteolysis occurs.

TABLE 1

Sample substrate sequences for protease

| | \multicolumn{8}{c|}{Protease} | |
|---|---|---|---|---|---|---|---|---|---|
| | N5 | N4 | N3 | N2 | N1 | N1' | N2' | N3' | N4' | Reference |
| Plasmin (SEQ ID NO: 5) | | | L | I | K | M | K | P | | 1 |
| Plasmin (SEQ ID NO: 6) | | | N | F | K | S | Q | L | | 1 |
| Stromelysin (SEQ ID NO: 7) | Ac | G | P | L | A | L | T | A | L | 2 |
| Stromelysin (SEQ ID NO: 8) | | Ac | P | F | E | L | R | A | NH$_2$ | 2 |
| Elastase (SEQ ID NO: 9) | | | Z- | A | A | F | A | NH$_2$ | | 3 |
| Collagenase (SEQ ID NO: 10) | | G | P | L | G | I | A | G | P | 4 |
| t-PA SEQ ID NO: 11) | P | H | Y | G | R | S | G | G | | 5 |
| u-PA (SEQ ID NO: 12) | P | G | S | G | R | S | A | S | G | 5 |

References:
1. Takagi and Doolittle, *Biochem.*, 14: 5149-5156 (1975).
2. Smith et al., *J. Biol. Chem.*, 270: 6440-6449 (1995).
3. Besson et al., *Analytical Biochemistry*, 237: 216-223 (1996).
4. Netzel-Arnett et al., *J. Biol. Chem.*, 266: 6747-6755 (1991).
5. Coombs et al., *J. Biol. Chem.*, 273: 4323-4328 (1998).

Enzymes that can be used for proteolytic degradation are numerous. Preferably, the cleavage site is cleavable by an enzyme, such as plasmin and matrix metalloproteinases.

In a preferred embodiment the sequence YKNR (SEQ ID NO: 13) is present between the first domain and the second domain. This sequence is plasmin degradable.

A preferred PTH fusion peptide is TGplPTH$_{1-34}$:

(SEQ ID NO: 14)
NQEQVSPLYKNRSVSEIQLMHNLGKHLNSMERVEWLRKKLQDVHNF.

Another preferred PTH fusion peptide is TG-PTH$_{1-34}$, which comprises the amino acids 1-34 of the native PTH as well as a TG (transglutaminase) substrate domain but no degradation site (SEQ ID NO: 15)
NQEQVSPLSVSEIQLMHNLGKHLNSMERVEWLRKKLQDVHNF.

ii. Hydrolytic Degradation Sites

Suitable non-enzymatic degradation substrates include any linkage that undergoes hydrolysis by an acid or base catalyzed mechanism. These substrates include oligo-esters, such as oligomers of lactic or glycolic acid. The rate of degradation of these materials can be controlled through the choice of oligomer. Preferably, the fusion peptide is included in the final mixture in a concentration range of between 0.01 to 2 mg/mL fibrin matrix, optionally from 0.01 to 1 mg/mL fibrin matrix or from 0.2 to 0.7 mg/mL fibrin matrix. The method is typically performed under sterile conditions. Preferably the components are pre-packed and mixed in a sterile manner. Thus, any infections due to contaminated products are avoided.

II. Kits

A kit of parts for producing a fibrin matrix according to the method as previously described is also disclosed. The kit comprises a first component including fibrinogen or a fibrinogen precursor and a transglutaminase or transglutaminase precursor, a second component including thrombin or a thrombin precursor and a third component including a fusion peptide comprising a first domain and a covalently crosslinkable transglutaminase substrate in a second domain. The kit may further comprise at least one connecting device for mixing the first component, the second component and third component. Such connecting device may be a separate device or may be a part of a container containing one of the components. The third component is provided separately from the first component and the second component.

By providing the third component separately from the first and second components any undesired contact between the components that may lead to degradation associated to incompatibility of the compounds is avoided. The kit further allows mixing of the components directly prior to use.

Preferably, the third component is provided in a container directly or indirectly connectable, or connected, to a connecting device. The container containing the third component may be aseptically packed or sterilized. Preferably a connecting device is also provided sterile.

The container can be a syringe, a vial, a cartridge or a bag made from material known in the art.

Mixing of the components is ensured without exposing the contents of the container and connecting device to the environment reducing risk of contamination.

The first component and the second component may be provided in separate containers, connectable to the connecting device. The connecting device may be constructed such that the container with the first component, the container with the second component and the container with the third component may be directly or indirectly connectable to the connecting device at the same time. Such connecting device may be a separate device or may be a part of a container containing one or more of the components.

The connecting device contains a sufficient number of openings to accommodate the number of containers and/or additional connecting devices that are needed for sufficient mixing of the components. Preferably, the connecting device comprises at least one slot, preferably one, two, or three slots. The slots are openings that may be disposed on one side of the connecting device or at opposing sides of the connecting device. The slots are configured such that the containers can be coupled to the connecting device, directly or indirectly. By direct connection or coupling it is meant that the container is attached to the connecting device via one of the slots. Indirect connection means that the container is connected to the connecting device via an additional connecting device, e.g. an adapter, a hose. The additional connecting device may be attached to one of the slots of the connecting device. The connecting device may also be part of one of the containers, such as located at the opening to the container with a suitable structure for connecting a second container to the container with the connecting device.

An adapter is a type of connecting device that is generally hollow and typically contains two openings on opposite sides of the adapter, where each opening has a suitable configuration for attaching to the opening of a container or an opening of another connecting device. Adapters are often used to indirectly connect a container to an opening of a connecting device, when the opening does not have a suitable configuration to attach directly to the opening in the container. For example, if an opening is in the shape of a nozzle, an adapter may be attached to the end to indirectly connect a container to the nozzle of the connecting device. Adapters can also be used to connect two containers to each other, with one container attached to one side of an adapter and the other container attached to the opposite side. Some adapters include a valve to open or close the adapter.

Connecting devices are generally hollow and contain openings. At least a first opening is suitable for attaching to device first container or a second connecting device and at least a second opening is suitable for attaching to a second container or a third connecting device. Optionally, a connecting device has openings for up to four containers to connect directly or indirectly to the connecting device. Optionally the connecting device has an opening through which the fibrin matrix exits the connecting device and is applied to the surface of a patient. Optionally, the connecting device includes a valve or mechanism to open and close one or both of the openings. Optionally, the connecting device includes a static mixer to facilitate mixing of the components. Optionally, the connecting device is part of a container that holds one or more components. In this embodiment, one end of the connecting device is attached directly to the container, for example one end of the connecting device can be integral with the container and serve as its opening.

By providing the components in separate containers (or in separate compartments in the same container or in separate compartments attached to a connecting device) any contamination or undesired pre-mixing of the components is avoided.

Alternatively, the first and the second components may be provided in separate compartments of a connecting device or in separate containers connected to a connecting device. A plunger that allows mixing of the first and second component may additionally be provided. The connecting device may further comprise a slot for connecting the container comprising the third component.

By already providing the first and second components in separate compartments of a connecting device or in separate containers connected to a connecting device, less packing material is required and any contamination that may occur due to erroneous filling of the connecting device is avoided.

Preferably, each component is in separate primary package, and the primary package of the first component, the primary package of the second component, the primary package of the third component, and the connecting device are sterile and sterile-packed. A primary package is the container or compartment that is in direct contact with a component.

A fibrin matrix containing a fusion peptide obtainable by a method as previously described for the use to generate bone or heal bone fractures is also disclosed.

The fusion peptide may comprise PTH a bioactive factor as previously described. The advantage of such a fibrin matrix can be found in enhanced bone healing capabilities to the release of a bioactive factor triggering bone formation.

Preferably, the fibrin matrix containing a fusion peptide as previously described may be used in the treatment of bone fractures, bone cysts or of a state of low bone density. Optionally, the fibrin matrix is used in the treatment of a bone in a patient with osteoporosis. The state of low bone density can be characterized by comparing the bone mineral density of particular bone type (e.g. spine, hip, etc.) of an individual to the norm for healthy 30-year-old adults. An individual with a bone having a bone density of more than 1 standard deviation below the mean for healthy 30-year-old adults is considered to have a low bone density. Using the same test, an individual is considered to have osteoporosis if any bone has a bone density of more than 2.5 standard deviations below the mean for a healthy 30-year old adult.

The fibrin matrix containing a fusion peptide as previously described may also be used in a procedure to fuse the two or more bones of a patient, for example to fuse segments of the spine of a patient undergoing a spinal fusion, or to fuse the ankle bones of a patient undergoing ankle fusion.

Exemplary embodiments are shown in the Figures.

FIG. 1 shows three mixing options for producing a fibrin matrix as described herein. In FIG. 1A, a first component 1 and a second component 2 are provided. The first component 1 comprises fibrinogen or a fibrinogen precursor and a transglutaminase or a transglutaminase precursor. The second component comprises thrombin or a thrombin precursor. The first component 1 and the second component 2 are mixed together to obtain mixture 4. To the mixture 4, a third component 3 comprising a fusion peptide with a first domain and a covalently crosslinkable transglutaminase substrate domain in a second domain is added to form the fibrin matrix 5.

Figure 1B:
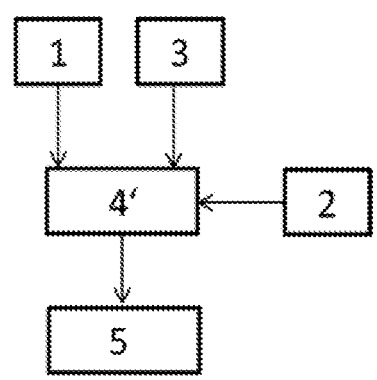
Figure 1C:
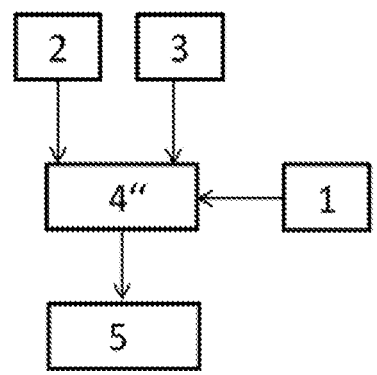

In FIGS. 1B and 1C, two orders of mixing the components are provided. In FIG. 1B, the first component 1 is mixed with the third component 3 resulting in a mixture 4'. To the mixture 4', the second component 2 is added forming the fibrin matrix 5. In FIG. 1C, the second component 2 and the third component 3 are mixed to obtain mixture 4". To the mixture 4", the first component 1 is added forming the fibrin matrix 5.

Independent of the sequence of mixing the first component 1, second component 2, and third component 3, the mixing time for all three components in FIGS. 1A, 1B, and 1C does not exceed 5 days.

Figure 2A:
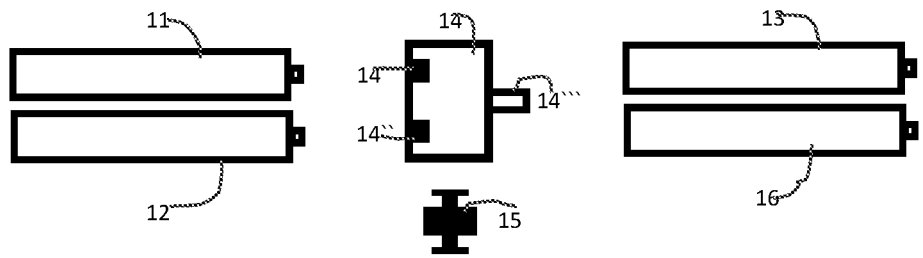
FIGS. 2A, 2B, 2C, 2D, and 2E are schematics of an exemplary embodiment of a kit of parts containing four containers (one containing each of the three components and one for the final mixture), a connecting device, and an adapter for use in the method described herein, according to the invention used in a method according to the invention.

In FIGS. 2A, 2B, 2C, 2D and 2E a kit of parts and its use in a method described herein are shown. The kit is shown in FIG. 2A and comprises a first container (11) comprising the first component and a second container (12) comprising the second component. A third container (13) comprising the third component is also provided. The first component comprises fibrinogen or a fibrinogen precursor and a transglutaminase or a transglutaminase precursor. The second component comprises thrombin or a thrombin precursor. The third component comprises a PTH fusion peptide, such as TGplPTH$_{1-34}$, wherein PTH$_{1-34}$ is the active factor of PTH in a truncated version, pl is a plasmin cleavage site and TG is a covalently crosslinkable transglutaminase substrate in a second domain. The kit further comprises a connecting device 14 with three slots 14', 14" and 14''' to which the three containers 11, 12 and 13 may be connected as further described in FIGS. 2B-2D. Additionally, empty container 16 and a second connecting device, such as an adapter 15, may be provided.

Figure 2B:
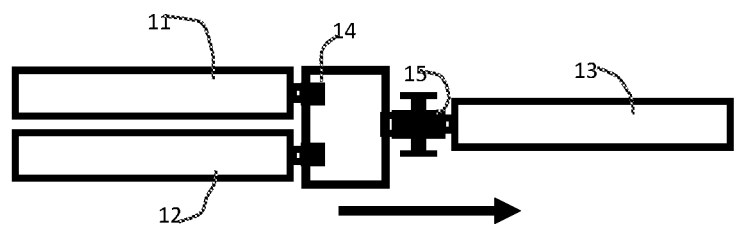

In FIG. 2B, a first way of connecting the containers is provided. Containers 11 and 12 are directly connected to the connecting device 14 via the respective slots 14' and 14". Container 13 is connected to slot 14''' of the connecting device by means of a second connecting device, such as an adapter 15. By simultaneous pushing of the contents of the containers 11 and 12 into connecting device 14 and through adapter 15, a mixture of the first and second components is transferred to the third component contained in container 13.

Figure 2C:
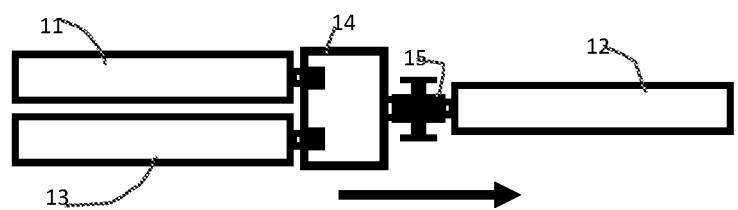

In FIG. 2C, a second way of connecting the containers is provided. Containers 11 and 13 are directly connected to the connecting device 14 via the respective slots 14' and 14". Container 12 is connected to slot 14''' of the connecting device by means of a second connecting device, such as an adapter 15. By simultaneous pushing of the contents of the containers 11 and 13 into connecting device 14 and through adapter 15 a mixture of the first and third component is transferred to the second component contained in container 12.

Figure 2D:
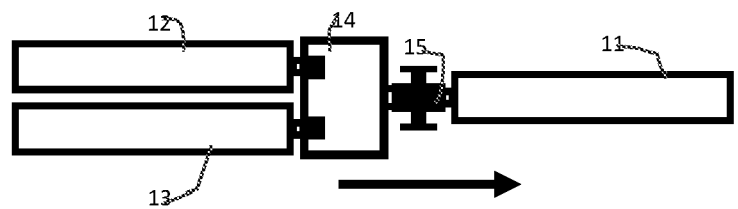

In FIG. 2D, a third way of connecting the containers is provided. Containers 12 and 13 are directly connected to the connecting device 14 via the respective slots 14' and 14". Container 11 is connected to slot 14''' of the connecting device by means of a second connecting device, such as an adapter 15. By simultaneous pushing of the contents of the containers 12 and 13 into connecting device 14 and through adapter 15 a mixture of the second and third component is transferred to the first component contained in container 11.

It is understood that containers 11 and 12 in FIG. 2B, containers 11 and 13 in FIG. 2C, and containers 12 and 13 in FIG. 2D may be provided as a two compartments in a single device, such as in the form of a double barrel syringe. The respective containers shown in in FIGS. 2B-2D may be indirectly connected to slot 14''' with a second connecting device, such as adapter 15 as shown in FIGS. 2B-2D. Alternatively, slot 14''' of the connecting device 14 may contain a second connecting device, such as an adapter, allowing it to directly connect with the respective containers. Moreover, the setups shown in FIGS. 2B-2D may be provided partly or fully preassembled in the kit.

Figure 2E:
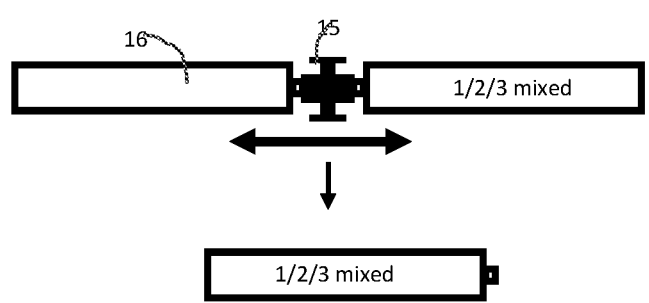

FIG. 2E depicts a method for further mixing the three components. Such further mixing may or may not be required. The method depicted in FIG. 2E depicts one but not the only method of further mixing. In the method, the connecting device 14 is replaced by an empty container 16 and by applying pressure to the container containing the mixture of the three components (container 13 for mixing method described in FIG. 2B, container 12 for mixing method described in FIG. 2C and container 11 for mixing method described in FIG. 2D) and its contents are pressed into container 16 to allow a better mixing of all components. The homogeneity of mixture of the three components may be increased by pushing the mixture between the two connected containers back and forth as indicated by the arrow.

Finally, the container (i.e. container 11, 12, 13, or 16, depending on the method used) containing the final mixture for forming the fibrin matrix is removed from the adapter 15 and its content is applied in situ in or on the body or outside the body.

In FIGS. 2B-2E the contents of the containers can be expelled using plungers or any other suitable mechanism for pushing the contents out of a container.

In FIGS. 3A, 3B, 3C, and 3D a kit of parts and its use in a method described herein are shown. The kit shown in FIG. 3A comprises a first container (11) comprising the first component and a second container (12) comprising the second component. A third container (13) comprising the third component is also provided. The first component comprises fibrinogen or a fibrinogen precursor and a transglutaminase or a transglutaminase precursor. The second component comprises thrombin or a thrombin precursor. The third component comprises a PTH fusion peptide, such as TGplPTH$_{1-34}$, wherein PTH$_{1-34}$ is the active factor of PTH in a truncated version, pl is a plasmin cleavage site and TG is a covalently crosslinkable transglutaminase substrate in a second domain. The kit further comprises a connecting device, such as an adapter 15.

Figure 3A:
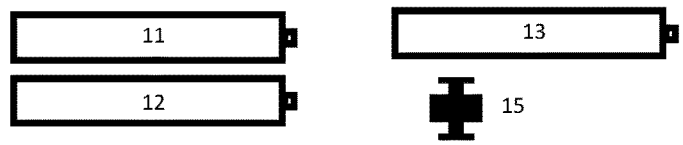
FIGS. 3A, 3B, 3C, and 3D are schematics of an exemplary embodiment of a kit of parts containing three containers (one containing each of the three components) and an adapter for use in the method described herein.
Figure 3B:
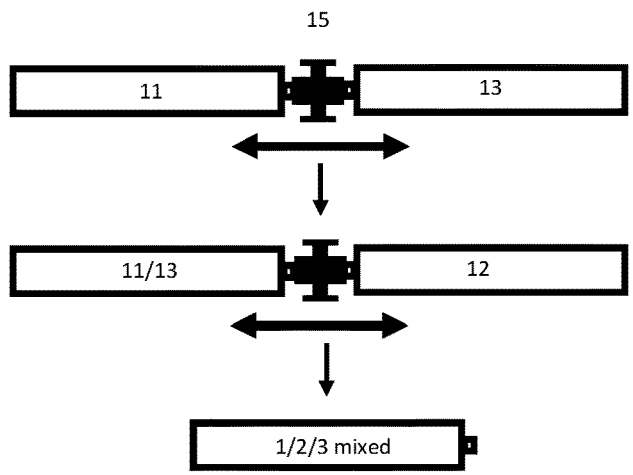

In FIG. 3B, a first method for mixing the contents of the containers is provided. Containers 11 and 13 are connected with a connecting device, such as adapter 15. The content of container 11 is transferred to container 13 (or vice versa) leading to the mixing of the contents of the two containers. The homogeneity of mixture of the two components may be increased by pushing the mixture between the two connected containers back and forth as indicated by the arrow. Then the container containing the mixture of the first and third components (i.e. either container 11 or container 13) is connected with adapter 15 to container 12 and the mixture of the first and third components is mixed with the second component. The homogeneity of mixture of the three components may be increased by pushing the mixture between the two connected containers back and forth as indicated by the arrow. Finally, the container containing the final mixture for forming the fibrin matrix is removed from the adapter 15 and its content is applied in situ in or on the body or outside the body.

Figure 3C:
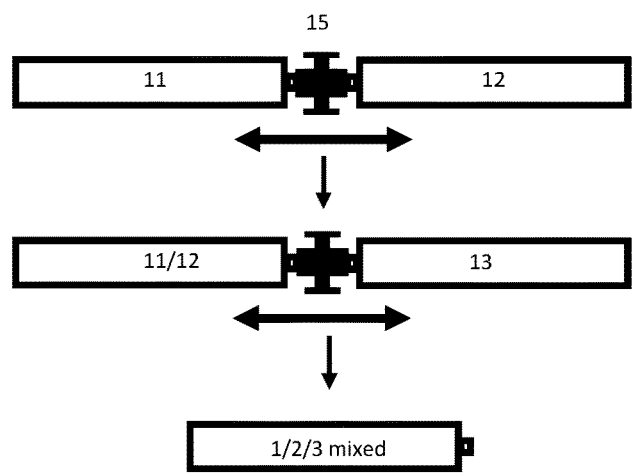

In FIG. 3C, a second method for mixing the contents of the containers is provided. Containers 11 and 12 are connected with a connecting device, such as adapter 15. The content of container 11 is transferred to container 12 (or vice versa) leading to the mixing of the contents of the two containers. The homogeneity of mixture of the two components may be increased by pushing the mixture between the two connected containers back and forth as indicated by the arrow. Then the container containing the mixture of the first and second components (i.e. either container 11 or container 12) is connected with adapter 15 to container 13 and the mixture of the first and second components is mixed with the third component. The homogeneity of mixture of the three components may be increased by pushing the mixture between the two connected containers back and forth as indicated by the arrow. Finally, the container containing the final mixture for forming the fibrin matrix is removed from the adapter 15 and its content is applied in situ in or on the body or outside the body.

Figure 3D:
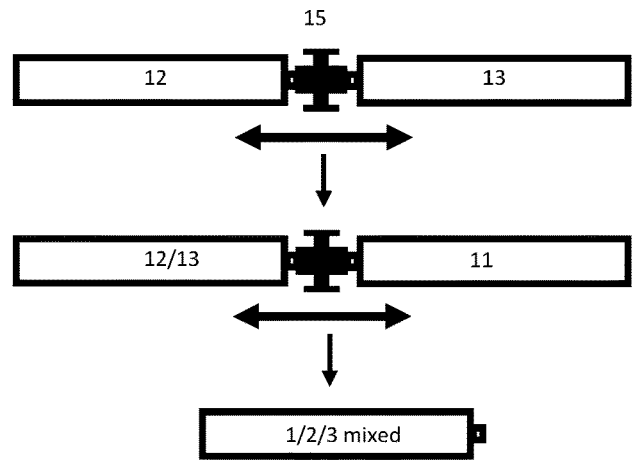

In FIG. 3D, a third method for mixing the contents of the containers is provided. Containers 12 and 13 are connected with a connecting device, such as adapter 15. The content of container 12 is transferred to container 13 (or vice versa) leading to the mixing of the contents of the two containers. The homogeneity of mixture of the two components may be increased by pushing the mixture between the two connected containers back and forth as indicated by the arrow. Then the container containing the mixture of the second and third components (i.e. either container 11 or container 13) is connected with adapter 15 to container 11 and the mixture of the second and third components is mixed with the first component. The homogeneity of mixture of the three components may be increased by pushing the mixture between the two connected containers back and forth as indicated by the arrow. Finally, the container containing the final mixture for forming the fibrin matrix is removed from the adapter 15 and its content is applied in situ in or on the body or outside the body.

In FIGS. 3B-3D the contents of the containers can be expelled using plungers or any other suitable mechanism for expelling the container. It is understood that the setups shown in FIGS. 3B-3D may be provided partly or fully preassembled in the kit.

In FIGS. 4A, 4B, 4C, and 4D a kit of parts and its use in a method described herein are shown. The kit shown in FIG. 4A comprises a first container (11) comprising the first component, a second container (12) comprising the second component, and a third container (13) comprising the third component. The first component comprises fibrinogen or a fibrinogen precursor and a transglutaminase or a transglutaminase precursor. The second component comprises thrombin or a thrombin precursor. The third component comprises a PTH fusion peptide, such as TGplPTH$_{1-34}$, wherein PTH$_{1-34}$ is the active factor of PTH in a truncated version, pl is a plasmin cleavage site and TG is a covalently crosslinkable transglutaminase substrate in a second domain.

Figure 4A:
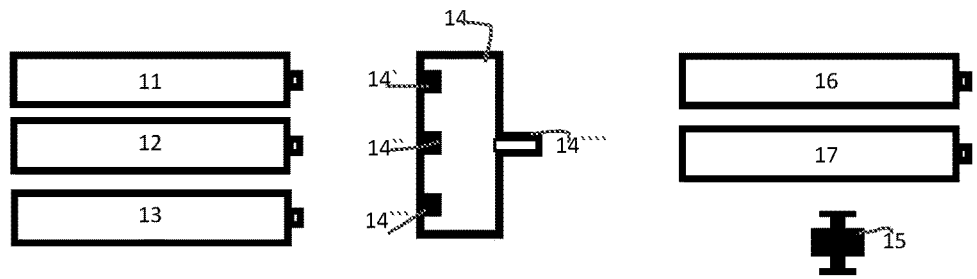
FIGS. 4A, 4B, 4C, and 4D are schematics of an exemplary embodiment of a kit of parts containing three containers (one containing each of the three components) and a connecting device for use in the method described herein. Optionally, the kit also contains one or two empty containers and a second commenting device, optionally an adapter, for further mixing of the three components.
Figure 4B:
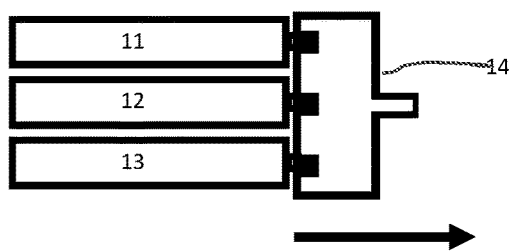

The kit further comprises a connecting device 14 with three slots (14', 14" and 14'") to which the three containers 11, 12 and 13 may be connected and a fourth slot 14"" to which an empty container may be connected directly or indirectly, or which can be used to release the mixture of the three components as depicted in FIG. 4B. Additionally, one or two empty container(s) 16 and/or 17 and a second connecting device, such as adapter 15, may be provide for further mixing of the three components.

In FIG. 4B, a method for mixing the contents of the containers is provided. Containers 11, 12 and 13 are directly connected to the connecting device 14 via the respective slots 14', 14" and 14'". By simultaneous pushing of the contents of the containers 11, 12 and 13 into connecting device 14 the first, second, and third components are mixed. The final mixture for forming the fibrin matrix may be applied through slot 14"" in situ in or on the body or outside the body. The contents of the containers can be expelled using plungers or any other suitable mechanism for pushing the contents out of a container.

Figure 4C:
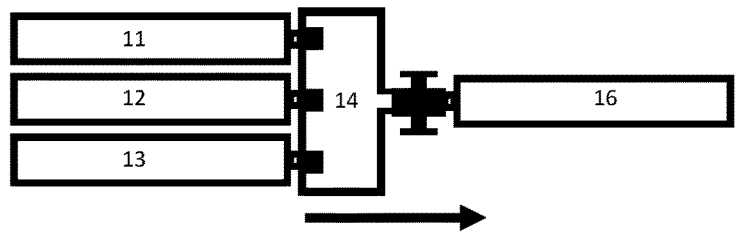

FIG. 4C depicts a method for further mixing of the three components. Such further mixing may or may not be required and the method depicted in FIG. 4C depicts one but not the only method of further mixing. In the method, an empty container 16 is connected to slot 14"" using a second connecting device, such as adapter 15, and by applying pressure to containers 11, 12 and 13 their contents are transferred through connecting device 14 to container 16. Container 16 containing a mixture of the three components may be removed from the connecting device and used to administer the final mixture for forming a fibrin matrix. The final mixture for forming the fibrin matrix may be applied through the opening in container 16 in situ in or on the body or outside the body. The contents of the container can be expelled using plungers or any other suitable mechanism for pushing the contents out of a container.

Figure 4D:
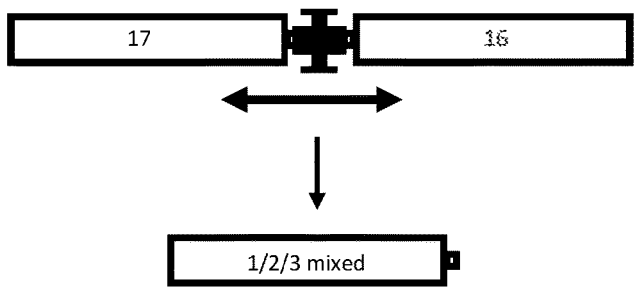

Optionally, as depicted in FIG. 4D, the connecting device is removed from the adapter, and empty container 17 is then connected with adapter 15. Thus, container 16 is attached to one end of adapter 15 and container 17 is attached to the opposite end of adapter 15. The homogeneity of mixture of the three components may be increased by pushing the mixture between the two connected containers back and forth as indicated by the arrow. Finally, the container containing the final mixture for forming the fibrin matrix (either container 16 or container 17) is removed from the adapter 15 and its content is applied in situ in or on the body or outside the body.

It is understood that containers 11, 12, and 13 in FIGS. 4A and 4B may be provided as a triple barrel syringe. Empty container 16 may either be indirectly connected to 14"" with adapter 15 as shown in FIG. 4C or slot 14"" of the connecting device 14 may itself be a suitably configured to directly connect container 16 to slot 14"" of the connecting device. Moreover, the setups shown in FIG. 4B may be provided partly or fully preassembled in the kit.

Figure 5A:
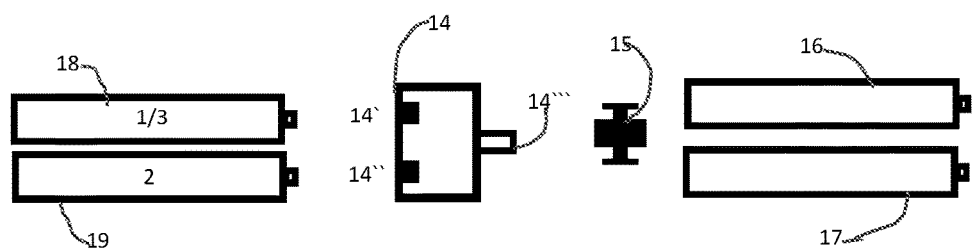
FIGS. 5A, 5B, 5C, 5D, 5E, 5F, and 5G are schematics of an exemplary embodiment of a kit of parts containing a first container comprising a mixture of the first and third components or the second and third components, and a second container comprising only the first component or only the second component. The kit also contains a connecting device and optionally, a second connecting device, such as an adapter, for use in the method described herein. Optionally, the kit also contains one or two empty containers (16 and 17) and a second connecting device, such as an adapter, for further mixing of the three components.
Figure 5B:
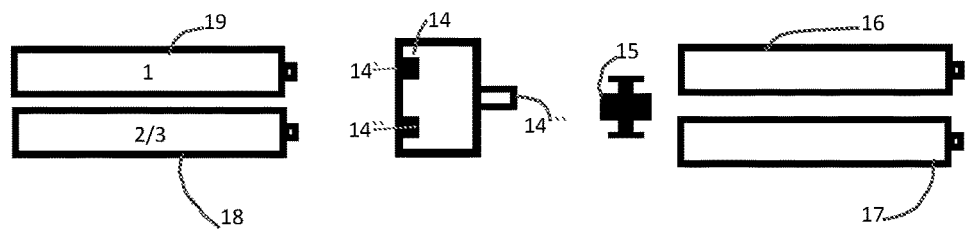

In FIGS. 5A, 5B, 5C, 5D, 5E, 5F, and 5G a kit of parts and its use in a method described herein are shown. Different forms of the kit are shown in FIGS. 5A and 5B. 5A shows a first kit comprising a first container 18 comprising a mixture of the first and third components (1/3) and a second container 19 comprising the second component (2). The first component comprises fibrinogen or a fibrinogen precursor and a transglutaminase or a transglutaminase precursor. The second component comprises thrombin or a thrombin precursor. The third component comprises a PTH fusion peptide, such as TGplPTH$_{1-34}$, wherein PTH$_{1-34}$ is the active factor of PTH in a truncated version, pl is a plasmin cleavage site and TG is a covalently crosslinkable transglutaminase substrate in a second domain. The kit may further comprise a connecting device 14 with three slots (14', 14" and 14'"), where the two containers 18 and 19 may be connected to two of the slots (14', 14") and an empty container 16 may be connected directly or indirectly to the third slot 14'", or the third slot 14'" can be used to release the mixture of the three components as further described in FIG. 5C. Additionally, one or two empty containers 16 and 17 and a second connecting device, such as adapter 15, may be provided for mixing or further mixing of the components as outlined in FIGS. 5D, and 5G.

FIG. 5B shows a second kit comprising a first container 19 comprising the first component (1) and a second container 18 comprising a mixture of the second and third components (2/3). The first component comprises fibrinogen or a fibrinogen precursor and a transglutaminase or a transglutaminase precursor. The second component comprises thrombin or a thrombin precursor. The third component comprises a PTH fusion peptide, such as TGplPTH$_{1-34}$, wherein PTH$_{1-34}$ is the active factor of PTH in a truncated version, pl is a plasmin cleavage site and TG is a covalently crosslinkable transglutaminase substrate in a second domain. The kit may further comprise a connecting device 14 with three slots (14', 14" and 14'"), where the two containers 18 and 19 may be connected to two of the slots (14', 14") and an empty container may be connected directly or indirectly to the third slot 14'", or the third slot 14'" can be used to release the mixture of the three components as further described in FIGS. 5C and 5E. Additionally, one or two empty container(s) 16 and 17 and a second connecting device, such as adapter 15, may be provided for mixing or further mixing of the components as depicted in FIGS. 5F and 5G.

Figure 5C:
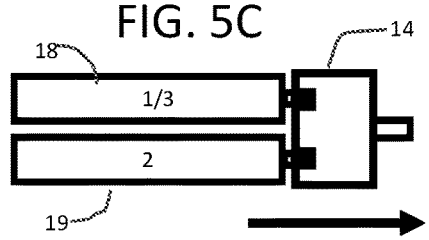

In FIG. 5C a first method for mixing the contents of the containers of the kit shown in FIG. 5A is provided. Container 18 containing the mixture (1/3) and container 19 containing the second component (2) are directly connected to the connecting device 14 via the respective slots 14' and 14". By simultaneous pushing of the contents of the containers 18 and 19 into device first connecting device 14 the first, second and third components are mixed. The final mixture for forming the fibrin matrix may be applied through slot 14'" in situ in or on the body or outside the body. Alternatively, the three components may be further mixed prior to the application as described in FIG. 5G.

Figure 5D:
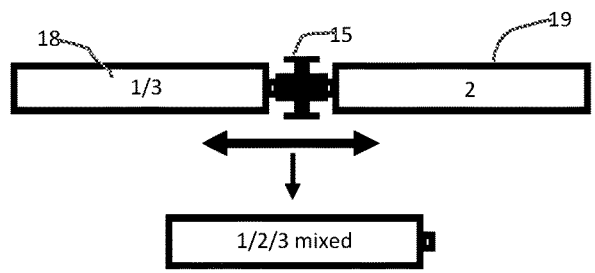

In FIG. 5D a second method for mixing the contents of the containers of the kit shown in FIG. 5A is provided. Container 18 containing the mixture (1/3) and container 19 containing the second component (2) are directly connected to each other using a connecting device, such as adapter 15. The content of container 18 is transferred to container 19 (or vice versa) leading to the mixing of the contents of the two containers. The homogeneity of mixture of the three components may be increased by pushing the mixture between the two connected containers back and forth as indicated by the arrow. Finally, the container containing the final mixture for forming the fibrin matrix is removed from the adapter 15 and its content is applied in situ in or on the body or outside the body.

Figure 5E:
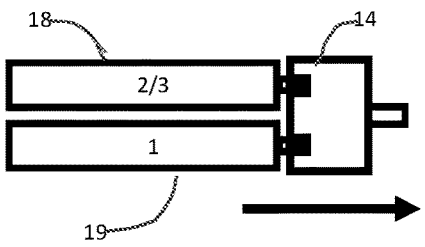
Figure 5F:
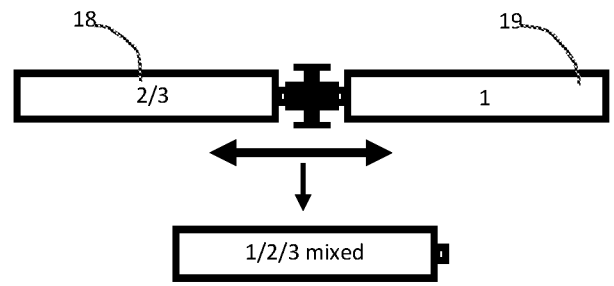
Figure 5G:
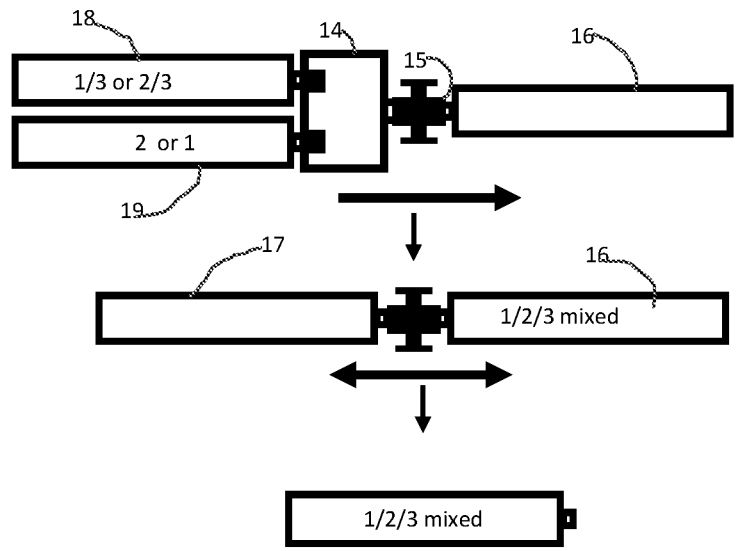

In FIG. 5E a first method for mixing the contents of the containers of the kit shown in FIG. 5B is provided. Container 18 containing the mixture (2/3) and container 19 containing the first component (1) are directly connected to the connecting device 14 via the respective slots 14' and 14". By simultaneous pushing of the contents of the containers 18 and 19 into connecting device 14 the first, second, and third components are mixed. The final mixture for forming the fibrin matrix may be applied through slot 14''' in situ in or on the body or outside the body. Alternatively, the three components may be further mixed prior to the application as described in FIG. 5G.

In FIG. 5F a second method for mixing the contents of the containers of the kit shown in FIG. 5B is provided. Container 18 containing the mixture (2/3) and container 19 containing the first component (1) are directly connected to each other using a connecting device, such as adapter 15. The content of container 18 is transferred to container 19 (or vice versa) leading to the mixing of the contents of the two containers. The homogeneity of mixture of the three components may be increased by pushing the mixture between the two connected containers back and forth as indicated by the arrow. Finally, the container containing the final mixture for forming the fibrin matrix is removed from the adapter 15 and its content is applied in situ in or on the body or outside the body.

FIG. 5G depicts a method for further mixing of the three components generated using the methods shown in FIGS. 5C and 5E. Such further mixing may or may not be required, and the method depicted in FIG. 5G depicts one but not the only method of further mixing. In the method, an empty container 16 is connected to slot 14''' using a second connecting device, such as adapter 15, and by applying pressure to containers 118 and 19 for the method shown in FIG. 5C or for the method shown in FIG. 5E and their contents are transferred through the first connecting device 14 to container 16. The first connecting device 14 is then removed from adapter 15, and empty container 17 is attached to adapter 15 in its place. Thus, container 16 containing a mixture of the three components is connected at one end to the second connecting device, such as adapter 15, and the second connecting device (e.g. adapter 15) is connected to empty container 17 at its opposite end. The homogeneity of mixture of the three components may be increased by pushing the mixture between the two connected containers back and forth as indicated by the arrow. Finally, the container containing the final mixture for forming the fibrin matrix is removed from adapter 15 and its content is applied in situ in or on the body or outside the body.

It is understood that containers 18 and 19 in FIGS. 5A and 5B may be provided as double barrel syringes. Empty container 16 may either be indirectly connected to 14''' with the second connecting device, such as adapter 15, as shown in FIG. 5G or alternatively, slot 14''' of the connecting device 14 may itself be suitably configured to directly connect container 16 to slot 14'''. Moreover, the setups shown in FIGS. 5C-5G may be provided partly or fully preassembled in the kit.

The contents of the containers can be expelled using plungers or any other suitable mechanism for mechanism for pushing the contents out of a container.

EXAMPLES

Example 1: Stability of TGplPTH$_{1-34}$ Over Time in Fibrinogen Stored at Room Temperature In order to evaluate the stability of TGplPTH$_{1-34}$ in the fibrinogen component over time, TGplPTH$_{1-34}$ was mixed with a fibrinogen solution and stored at room temperature.

TGplPTH$_{1-34}$ was added to fibrinogen solution at a concentration of 266 µg/ml and incubated at room temperature for up to 34 days. Samples were taken at indicated time points and TGplPTH$_{1-34}$ concentration was determined by HPLC. Briefly, TGplPTH$_{1-34}$ was quantified with a HPLC-UV method using a Zorbax Agilent RP18 column (4.6×150 mmm, 5 µm, 300 A) for the separation of related substances. As eluent A: 0.1% TFA, 1% ACN in water and as eluent B: 0.1% TFA in ACN was used. The gradient was 0 min. 26% B; 15 min 38% B; 18 min. 90% B; 22 min 26% B; 24 min 26% B. The injection volume was 20 µl and the flow rate was 1 ml/min. The column temperature was 35° C. A reference standard was used for the calibration curve.

The results from the TGplPTH$_{1-34}$ stability analysis in fibrinogen stored at room temperature (20-25° C.) for up to 34 days are shown in Table 2.

TABLE 2

| Time points (day) | Number of samples (two measures each) | TGplPTH$_{1-34}$ content Mean ± SD (µg/ml) | % loss of TGplPTH$_{1-34}$ |
|---|---|---|---|
| 0 | 3 | 232 ± 0.99 | |
| 3 | 2 | 222 ± 0.80 | −4.3 |
| 5 | 2 | 214 ± 1.48 | −7.8 |
| 7 | 2 | 208 ± 1.76 | −10.3 |
| 14 | 2 | 192 ± 2.28 | −17.2 |
| 21 | 2 | 176 ± 1.57 | −24.1 |
| 29 | 2 | 172 ± 2.51 | −25.9 |
| 34 | 2 | 167 ± 1.2 | −28.0 |

As shown in Table 2, TGplPTH$_{1-34}$ was rapidly degraded when exposed to fibrinogen solution at room temperature. Already 4.3-7.8% of the product are degraded in the time frame need for the manufacturing (3-5 days) of the fibrin sealant. After 5 days, the amount of degraded products reaches a level that is outside the acceptable range for final product application. TGplPTH$_{1-34}$ cannot be mixed with fibrinogen and used more than 5 days after mixing in the process used for manufacturing of the fibrin sealant.

Example 2: Comparison of Covalent Binding of TGplPTH$_{1-34}$ to Fibrin Using Different Methods of Preparation The percentage of covalent TGplPTH$_{1-34}$ binding to fibrin matrices was determined in fibrin matrices prepared with two different methods using an indirect assay. With this assay, non-covalently bound TGplPTH$_{1-34}$ that can be washed out of the matrix is determined. In the first method (pre-mixing), the two components of the fibrin sealant, ARTISS® were thawed and TGplPTH$_{1-34}$ was premixed with the fibrinogen component at a concentration of 2 mg/ml. Immediately after mixing, the two components of the fibrin sealant were frozen again and stored at −20° C.

The samples were then thawed, and the two components of the sealant were mixed. The final concentration of TGplPTH$_{1-34}$ in mixed fibrin sealant was 1 mg/ml.

In the second method, the two fibrin sealant components were directly mixed with TGplPTH$_{1-34}$ solubilized in water to achieve a final concentration of 1 mg/ml (see FIG. 1A).

To evaluate the amount of TGplPTH$_{1-34}$ covalently bound to the fibrin matrix with the two methods, samples prepared by either of the two methods were subjected to a retention assay. Aliquots of 50 μl were added to 1.5 ml Eppendorf tubes. The fibrin matrices were then incubated at 37° C. for 1 hour. Unbound TGplPTH$_{1-34}$ was extracted from the fibrin matrix by addition of 1.5 ml extraction buffer (50 mM Tris pH 9.4, 1M NaCl, 0.1% Tween 20) supplemented with protease Inhibitors (Roche Cat #11836153001 cOmplete™, Mini Protease Inhibitor Co) and incubated under constant shaking. After 3 hours the supernatant was collected and 1.5 ml of fresh extraction buffer was added to the fibrin matrix. This extraction step was repeated after 6, 24, 30 and 48 h. Collected supernatants were stored at −20° C. until further processing.

To determine the amount of unbound TGplPTH$_{1-34}$, the 5 collected supernatants were thawed and pooled. TGplPTH$_{1-34}$ in the pool was determined by ELISA with a commercial PTH$_{1-34}$ ELISA kit (Immutopics, Cat *60-3900) following the manufacturer's recommendation. Two independent experiments (three samples per fibrin matrix and experiment) were performed with both preparation methods and the amount of TGplPTH$_{1-34}$ not bound to the fibrin matrix was determined.

The results for these experiments are shown in Table 3.

TABLE 3

% unbound TGplPTH$_{1-34}$ in fibrin matrices produced with different methods

| | Experiment 1 | | | Experiment 2 | | | Average % |
|---|---|---|---|---|---|---|---|
| Sample | 1 | 2 | 3 | 1 | 2 | 3 | unbound ± SD |
| First method | 16.8 | 14.4 | 13.9 | 14.7 | 10.2 | 15.1 | 14.2 ± 2.2 |
| Second method | 13.9 | 11.3 | 15.4 | 14.4 | 14.4 | 14.7 | 14.0 ± 1.4 |

As shown in Table 3, it was surprisingly found that very similar amounts were not bound to fibrin matrix with both methods used. Hence both mixing methods lead to similar binding of TGplPTH$_{1-34}$ to the fibrin matrix.

---

We claim:

1. A method for forming a fibrin matrix comprising a fusion peptide, wherein the method comprises the steps of:
   i) providing a first component comprising fibrinogen or a fibrinogen precursor and a transglutaminase (TG) or a transglutaminase precursor,
   ii) providing a second component comprising thrombin or a thrombin precursor, wherein neither the first component nor the second component comprises a fusion peptide comprising a first domain and a covalently crosslinkable transglutaminase substrate domain in a second domain,
   iii) providing a third component comprising the fusion peptide, wherein the third component does not contain fibrinogen, a fibrinogen precursor, thrombin, nor a thrombin precursor,
   iv) mixing the first and second components to form a mixture of the first and second components, and
   v) adding the third component to the mixture of step iv) within 5 minutes or less after mixing the first and second components.

2. The method of claim 1, wherein the fusion peptide comprises parathyroid hormone (PTH) in the first domain.

3. The method of claim 2, wherein PTH is selected from the group consisting of PTH1-84, PTH1-38, PTH1-34, PTH1-31, and PTH1-25.

4. The method of claim 1, wherein the first component or the second component further comprises a calcium ion source.

5. The method of claim 1, wherein in step (iv), the fusion peptide is added in a concentration range of 0.01 to 2 mg/mL fibrin matrix.

6. The method of claim 1, wherein the first component comprises a transglutaminase precursor and wherein the transglutaminase precursor is Factor XIII.

7. The method of claim 1, wherein the fusion peptide further comprises a degradation site between the first and second domains.

8. The method of claim 7, wherein the degradation site is an enzymatic cleavage site.

9. The method of claim 8, wherein the enzymatic cleavage site is a plasmin cleavage site.

10. The method of claim 1, wherein the method is performed under sterile conditions.

11. The method of claim 1, further comprising (v) (vi) administering the mixture of step (v) to a patient at a site in need of bone generation, of a bone cyst, or of a bone fracture.

12. The method of claim 11, wherein the site in need of bone generation is a bone in a state of low bone density.

13. The method of claim 11, wherein the site in need of bone generation is in the spine and the patient is undergoing a spinal fusion.

14. The method of claim 11, wherein step (vi) occurs within 5 days of initiating step (iv).

15. The method of claim 1, wherein less than 7.8% of the fusion peptide degrades during step (v).

16. The method of claim 1, wherein less than 4.3% of the fusion peptide degrades during step (v).

17. The method of claim 1, wherein step (v) occurs during step (iv).

18. The method of claim 1, wherein step (v) occurs within 30 seconds of initiating step (iv).

19. The method of claim 1, wherein the first component is provided in a first container or compartment, wherein the second component is provided in a second container or compartment, and wherein the third component is provided in a third container or compartment,
   wherein during steps (iv) and (v) the first, second, and third containers or compartments are attached directly or indirectly to a connecting device.

20. The method of claim 19, wherein the connecting device comprises a static mixer.

21. The method of claim 19,
   wherein the first container or compartment and the second container or compartment are attached to the same side of the connecting device, and
   wherein the third container is attached to the opposite side of the connecting device.

22. The method of claim 21, wherein the first and second containers or compartments are two compartments in a double barrel syringe.

23. The method of claim 21, wherein during steps (iv) and (v), the contents of each of the first and second containers or compartments are pushed out of the first and second containers or compartments through the connecting device and into the third container.

24. The method of claim 23, further comprising separating the connecting device from the first and second containers or compartments and attaching a fourth container or compartment, directly or indirectly, to the connecting device, wherein the connecting device is attached directly or indirectly to the third container or compartment, and wherein the fourth container or compartment is empty.

25. The method of claim 24, further comprising mixing the first, second, and third components by (a) pushing the contents of the third compartment into the fourth compartment and (b) then pushing the contents of the fourth compartment into the third compartment, and repeating steps (a) and (b).

26. The method of claim 23, further comprising separating the third container or compartment from the connecting device and attaching a fourth container or compartment, directly or indirectly, to the third container or compartment via a second connecting device, wherein the fourth container or compartment is empty.

27. The method of claim 26, further comprising mixing the first, second, and third components by (a) pushing the contents of the third compartment into the fourth compartment and (b) then pushing the contents of the fourth compartment into the third compartment, and repeating steps (a) and (b).

* * * * *